(12) United States Patent
Horstmann et al.

(10) Patent No.: US 9,717,698 B2
(45) Date of Patent: *Aug. 1, 2017

(54) TRANSDERMAL THERAPEUTIC SYSTEM WITH HIGH RATE OF UTILIZATION OF ACTIVE SUBSTANCE AND DOSING ACCURACY

(71) Applicant: LTS Lohmann Therapie-Systeme AG, Andernach (DE)

(72) Inventors: Michael Horstmann, Neuwied (DE); Walter Mueller, Andernach (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/216,446

(22) Filed: Jul. 21, 2016

(65) Prior Publication Data

US 2016/0324799 A1 Nov. 10, 2016

Related U.S. Application Data

(63) Continuation of application No. 14/709,126, filed on May 11, 2015, now Pat. No. 9,421,174, which is a continuation of application No. 12/515,630, filed as application No. PCT/EP2007/009707 on Nov. 9, 2007, now Pat. No. 9,056,026.

(30) Foreign Application Priority Data

Nov. 21, 2006 (DE) ......................... 10 2006 054 733

(51) Int. Cl.
| | |
|---|---|
| *A61K 9/70* | (2006.01) |
| *A61F 13/02* | (2006.01) |
| *A61L 15/44* | (2006.01) |
| *A61K 31/4468* | (2006.01) |

(52) U.S. Cl.
CPC ............ *A61K 9/7061* (2013.01); *A61F 13/02* (2013.01); *A61F 13/0233* (2013.01); *A61F 13/0246* (2013.01); *A61K 9/7053* (2013.01); *A61K 9/7084* (2013.01); *A61K 31/4468* (2013.01); *A61L 15/44* (2013.01); *A61L 2300/402* (2013.01)

(58) Field of Classification Search
CPC .. A61F 13/02; A61F 13/0233; A61F 13/0246; A61K 9/7084; A61K 9/7061; A61K 9/7053; A61K 31/4468; A61L 15/44; A61L 2300/402
See application file for complete search history.

(56) References Cited

U.S. PATENT DOCUMENTS

| | | | |
|---|---|---|---|
| 4,769,028 A | 9/1988 | Hoffmann et al. | |
| 5,240,711 A | 8/1993 | Hille et al. | |
| 6,090,405 A | 7/2000 | Ninomiya et al. | |
| 9,056,026 B2 * | 6/2015 | Horstmann | ............ A61F 13/02 |
| 9,421,174 B2 * | 8/2016 | Horstmann | ............ A61F 13/02 |
| 2003/0099695 A1 | 5/2003 | Mueller | |
| 2003/0199807 A1 | 10/2003 | Dent et al. | |
| 2004/0071764 A1 | 4/2004 | Bracht | |
| 2004/0096490 A1 | 5/2004 | Bracht et al. | |
| 2004/0234584 A1 | 11/2004 | Muller et al. | |
| 2005/0037059 A1 | 2/2005 | Miller, II | |
| 2005/0202073 A1 | 9/2005 | Jackson et al. | |
| 2006/0078600 A1 | 4/2006 | Muller | |
| 2006/0078604 A1 | 4/2006 | Kanios et al. | |
| 2007/0298091 A1 | 12/2007 | Kugelmann et al. | |
| 2007/0298961 A1 | 12/2007 | Rice et al. | |

FOREIGN PATENT DOCUMENTS

| | | |
|---|---|---|
| CA | 2 630 675 | 8/2007 |
| DE | 3315272 | 10/1984 |
| DE | 100 12 908 | 10/2001 |
| DE | 100 54 479 | 5/2002 |
| DE | 101 03 860 | 8/2002 |
| DE | 101 10 391 | 9/2002 |
| DE | 10 2004 003 224 | 8/2004 |
| DE | 10 2005 011 517 | 9/2006 |
| DE | 10 2006 026 060 | 7/2007 |
| EP | 1 137 406 | 7/1999 |
| WO | WO 02/41878 | 5/2002 |
| WO | WO 02/069940 | 9/2002 |
| WO | WO 03/018075 | 3/2003 |
| WO | WO 03/097020 | 11/2003 |

OTHER PUBLICATIONS

Allan et al. ("Randomised crossover trial of transdermal fentanyl and sustained release oral morphine for treating chronic non-cancer pain" in BMJ., vol. 322, May 12, 2001).
Muijsers et al. ("Transdermal Fentanyl: An Updated Review of its Pharmacological Properties and Therapeutic Efficacy in Chronic Cancer Pain Control" in Drugs, vol. 61, No. 15, 2001, abstract).
International Preliminary Report on Patentability.

* cited by examiner

*Primary Examiner* — Blessing M Fubara
(74) *Attorney, Agent, or Firm* — Haug Partners LLP

(57) ABSTRACT

A transdermal therapeutic system for administering at least one active pharmaceutical ingredient, including a polymer-based layer which is remote from the skin with a rate of application of at least 80 g/m$^2$, and an adhesive skin-contact layer which is adjacent to the polymer-based layer remote from the skin and is based on acrylate copolymers with a rate of application of not more than 50 g/m$^2$. The at least one active pharmaceutical ingredient is present in both the polymer-based layer remote from the skin and the skin-contact layer.

22 Claims, No Drawings

TRANSDERMAL THERAPEUTIC SYSTEM WITH HIGH RATE OF UTILIZATION OF ACTIVE SUBSTANCE AND DOSING ACCURACY

The present application is a continuation of U.S. patent application Ser. No. 14/709,126 filed on May 11, 2015, which is a continuation of U.S. parent application Ser. No. 12/515,630 filed on May 20, 2009, which claims priority from PCT Patent Application No. PCT/EP2007/009707 filed on Nov. 9, 2007, which claims priority from German Patent Application No. DE 10 2006 054 733.0 filed on Nov. 21, 2006. The disclosures of U.S. parent application Ser. Nos. 14/709,126 and 12/515,630 are incorporated herein by reference in their entirety.

Transdermal therapeutic systems (TTS) have been introduced into therapy for a number of years. For reference to the use in particular in the area of pain therapy, reference is made to the literature (B. Asmussen, Transdermale Therapeutische System-Eigenschaften and Anwendungen; In: Likar, Rudolf: Praxis der transdermalen Schmerztherapie, $1^{st}$ edition-Bremen 2002).

A number of active ingredients have been introduced in recent years into transdermal therapy in particular for highly active active ingredients with daily doses below 30 mg, or even below 5 mg: nicotine, fentanyl, buprenorphine, nitroglycerin, estradiol, rotigotine, to mention just a few examples. Flat systems using at least one of the polymer groups of silicone polymers, polyisobutylene adhesive compositions or polyacrylate adhesive compositions have been used for all these substances. Because of the favorable opportunities of responding to the requirements of active ingredients through appropriate derivatization, and because the adhesion to the skin is generally sufficient without further additives, acrylate polymers are particularly preferably used for transdermal therapeutic systems. Examples thereof are in particular the newly introduced Durogesic SMAT®, and numerous generic fentanyl TTS which were launched on the market in 2005 and 2006 by the companies Ratiopharm and Hexal in Germany. However, other active ingredients have also preferably been made available on the human skin with the polymeric principle of acrylic acid copolymer. Thus, transdermal therapeutic systems with nicotine (Nicotinel®-TTS), buprenorphine (Transtec®, Grünenthal) and estradiol (Estraderm MX®, Novartis) have successfully been launched on the market.

System structures of such transdermal systems comprise one or more layers, particular attention being paid in earlier years in particular to the aspect of the control of supply by the systems themselves. Typical structures in earlier times therefore provided a separation into adhesive layer, membrane layer and reservoir layer, with the essential proportion of active ingredient being present in the reservoir layer.

It is common to all these systems that it is frequently possible to administer transdermally only a very small part of the active ingredient available, and thus the so-called system utilization rate is relatively low. This is particularly important for transdermal therapeutic systems which comprise costly active ingredients, especially novel synthetic active ingredients such as rotigotine, fentanyl, buprenorphine or sufentanil.

The requirement to achieve a high rate of utilization of active ingredient is opposed by the requirement of a large layer thickness (application rate) of the adhesive layers and reservoir layers, which is necessary for the adhesiveness and producibility, and by the property of most adhesive compositions of dissolving a large proportion of active ingredient before the high thermodynamic activity (close to the saturation solubility) necessary for transdermal use is reached.

The requirement of large layer thicknesses together with high saturation solubilities of the active ingredients in the polymers is the cause of the unfortunately undesirably large use of active ingredients in most transdermal therapeutic systems. Mention may be made by way of example for the prior art in the area of transdermal systems with restricted utilization of active ingredients for example of U.S. Pat. No. 5,240,711, which describes polyacrylate matrices with 0.1-20% buprenorphine base with addition of further constituents. U.S. Pat. No. 6,090,405 describes transdermal systems for buprenorphine which comprise an acrylate copolymer and, contained therein, crosslinked acrylic polymer particles. WO 03/018075 describes a transdermal therapeutic system with fentanyl or related substances as active ingredient, which comprises a matrix layer based on polyacrylate. On the grounds of increasing the rate of utilization of active ingredient, in this case a copolymer free of acrylic acid groups is selected because the solubility, promoted by ion pair effects, of fentanyl and similar active ingredients is otherwise increased too greatly by carboxyl groups.

WO 03/097020 describes a two-layer system in which the layer on the skin side has a lower affinity for active ingredient than the layer remote from the skin and simultaneously has a larger layer thickness.

The objective according to the technical teaching of this publication is to achieve a constant delivery rate over lengthy periods of time. A lower rate of utilization due to active ingredient remaining in the layer remote from the skin, which dissolves better, is thus certainly further accepted.

EP 1 137 406 B1 describes a patch for transdermal administration of volatile active ingredients, especially nicotine. The patch has two layers, the layer remote from the skin consisting of an active ingredient-containing silicone adhesive material, the skin-contact layer consisting of an acrylic adhesive, and both layers having approximately the same thickness. It is pointed out that, after the lamination and reaching of an equilibrium, the acrylic adhesive layer likewise contains part of the active ingredient, specifically about 2.5 to 3.0% by weight.

Besides the economic factors described above, also very important are increasingly restrictive requirements of the approval authorities for the accuracy of dosage of transdermal therapeutic systems. Thus, coating accuracies with a standard deviation of about +/−5 $g/m^2$ can certainly be achieved with metering methods which can be carried out economically. With the weights per unit area which are customary in the art, of about 50-100 $g/m^2$, accordingly the variations in the coating accuracy and later the active ingredient content of the cut-out TTS are in the range between 5 and 10%. This accuracy has certainly been sufficient in pharmaceutical approval procedures to date. However, with the 2005 revision of the European Pharmacopoeia Monograph, accuracies with up to a standard deviation of below 3% are required if the median of the layer weight reached differs by up to 10% from the required value. This requirement thus makes it no longer economically possible to coat with layer thicknesses of about 50 $g/m^2$, e.g. according to the teaching of WO 03/018075, a monolithic polyacrylate system with an active ingredient content of 5%, because the described system would be unlikely to receive pharmaceutical approval by the authorities in terms of the accuracy of dosage.

On the other hand, the person skilled in the art prefers polymers which dissolve well and adhere well for adhesion to the skin in order to improve the acceptance and bioavailability of such systems. Polymers adhering to the skin which have emerged as ideal in recent years are polyacrylates which, however, have the disadvantage of a high dissolving capacity for the active pharmaceutical ingredients which are normally suitable for transdermal therapy.

It is therefore an object of the present invention to provide a transdermal therapeutic system with an acrylate copolymer skin-contact layer, with a rate of active ingredient utilization which is improved by comparison with the prior art, and with an accuracy of dosage which is increased by comparison with the prior art.

The object is achieved according to the invention by providing a transdermal therapeutic system (TTS) comprising a backing layer which is essentially impermeable for the active ingredient, a layer which is remote from the skin and is based on polyisobutylenes, an adhesive skin-contact layer based on acrylate copolymers which is thinner than the layer remote from the skin and, after production of the TIS, comprises the predominant part of the active ingredient, and a detachable protective layer which is essentially impermeable for the active ingredient. The coating weight of the layer remote from the skin is according to the invention at least 80 g/m$^2$, preferably 100-200 g/m$^2$; the coating weight of the skin-contact layer is according to the invention not more than 50 g/m$^2$, preferably 20-30 g/m$^2$.

In a preferred embodiment, the ratio of the coating weight of the layer remote from the skin to that of the skin-contact layer is at least 2:1, particularly preferably from 3:1 to 5:1. Although the polyisobutylene connected as basis of the layer remote from the skin has a lower diffusibility than the polysiloxane used in the prior art, it surprisingly emerges that the transdermal therapeutic system of the invention is superior to the systems known in the prior art in terms of the rate of utilization of active ingredient and dosage accuracy.

The TTS described above can be produced in the following way:

The active ingredient or the active ingredient mixture is dissolved in a suitable volatile solvent or in a mixture of such solvents, the resulting solution is mixed with the polymer composition which is intended for the layer remote from the skin and is based on polyisobutylenes, and the resulting mixture is applied uniformly in a layer thickness of at least 200 μm (corresponding to 200 g/m$^2$) to a suitable substrate, for example a siliconized plastic layer. After drying and evaporation of the solvent contents, the active ingredient-containing polymer layer is covered with a further sheet which represents the later backing layer of the TTS of the invention. After removal of the plastic sheet serving as substrate, an active ingredient-free adhesive skin-contact layer based on acrylate copolymers, and a detachable protective sheet is laminated onto the resulting laminate in such a way that the active ingredient-containing layer remote from the skin and the adhesive skin-contact layer are in contact with one another. After the diffusion equalization which starts immediately, most of the active ingredient(s) migrates out of that remote from the skin into the skin-contact layer.

The invention described above makes it possible for the dosage of the active ingredient or active ingredients to be very accurate and efficient through the introduction of the latter into the polymer composition of polyisobutylenes which, on the one hand, is applied in a relatively large layer thickness and, on the other hand, exhibits a very low dissolving capacity for the active ingredients used according to the invention, and for the accuracy on coating a sheet with the active ingredient/polymer mixture to be very high because of the relatively great layer thickness. Further advantages emerge from the fact that the adhesive skin-contact layer based on acrylate copolymers need not be coated with the active ingredient(s), so that the thickness of this layer is reduced below the coating weight of over 50 g/m$^2$, which is customary according to the previous prior art and is necessary for accurate dosage, and preferably can even be restricted to a typical rate of application of 20-30 g/m$^2$.

A polyethylene terephthalate sheet optionally coated with a polyisobutylene, a polyacrylate or polysiloxane serves as backing layer which is essentially impermeable for the active ingredient(s).

The matrix layer (skin-contact layer) which is in contact with the skin consists of acrylate copolymers. By this are meant copolymers of monomeric acrylic acid, methacrylic acid and/or suitable derivatives and optionally monomeric vinyl compounds. The following monomers may be mentioned by way of example: acrylic acid, methacrylic acid, acrylic esters and methacrylic esters, e.g. in particular n-butyl acrylate, n-butyl methacrylate, ethyl acrylate, 2-ethylhexyl acrylate, ethyl methacrylate, methyl acrylate, methyl methacrylate, tert-butyl acrylate, sec-butyl acrylate, tert-butyl methacrylate, cyclohexyl methacrylate, 2-ethylhexyl methacrylate, isobornyl methacrylate, isobutyl methacrylate, isopropyl acrylate, isopropyl methacrylate and mixtures of these monomers. These monomers are esters of acrylic or methacrylic acid which have linear, branched or cyclic aliphatic C1-C12 substituents. These substituents may in turn be substituted for example by hydroxy groups. Esters which may be mentioned by way of example are 2-hydroxyethyl methacrylate, 3-hydroxypropyl acrylate and 3-hydroxypropyl methacrylate. Vinyl acetate may be mentioned as a suitable vinyl compound.

Active ingredients suitable for the purposes of the present invention are in particular those which have high activity. The person skilled in the art generally understands by this active ingredients whose daily dose is in the mg range, e.g. 1-500 mg. However, active ingredients preferred according to the invention are those whose daily dose does not exceed 30 mg.

Suitable active ingredients for use in the TTS of the invention are for example analgesics, bronchodilators, antidiabetics, vasodilators, anticraving agents and antiparkinson agents.

However, the TTS of the invention is particularly suitable for pain therapy, preferably with active ingredients from the group of opioids. This group of active pharmaceutical ingredients includes inter alia morphine, heroin and further morphine derivatives; dihydromorphine derivatives such as hydromorphone (dihydrocodeine), oxycodone; morphine derivatives such as levorphanol, buprenorphine; analgesics of the pethidine group such as pethidine, ketobemidone, loperamide, diphenoxylate; methadone and derivatives such as levomethadone, dextromoramite, dextropropoxyphene; fentanyl and its derivative (e.g. alfentanil, sufentanil, remifentanil), benzomorphan derivatives such as pentazocine and phenylaminocyclohexynyl derivatives such as tilidine; tramadol. Particularly preferred for the treatment of breakthrough pain are fast- and short-acting opioids such as morphine, tramadol, tilidine, oxycodone, hydromorphone, buprenorphine, fentanyl and levomethadone.

Further suitable examples from the group of analgesics are the following: metamizole, phenazone, propyphenazone, flupirtine, nefopam, and from the group of antiepileptics are carbamazepine, gabapentine, clonazepam, also antidepressants such as amitryptiline.

The invention also includes the use of active ingredient combinations consisting of two or more medicinal substances, especially combinations of the aforementioned analgesics.

The polymer layers, preferably the skin-contact layer of the TTS of the invention, may further comprise various excipients or additives, for example from the group of solubilizers, solvents, plasticizers, tackifiers, permeation improvers, pH regulators, antioxidants and preservatives.

The invention is explained below by means of examples:

EXAMPLE 1

A solution of polyacrylic acid-co-2-ethylhexyl acrylate-co-vinyl acetate, 30% (w/w) in ethyl acetate is coated in a layer thickness of about 65-70 μm onto a siliconized polyethylene terephthalate sheet (100 μm thick) and dried in the open at 25° C. for 2 hours to result in an adhesive layer of 20 g/m$^2$. In a separate operation, 2 g of fentanyl base, 70 g of polyisobutylene 100, 28 g of polyisobutylene 10, 100 g of methyl ethyl ketone and 200 g of n-heptane are made into a viscous solution and then stirred for 2 hours. This phase is coated with a layer thickness of about 500 μm onto a 15 μm thick sheet of polyethylene terephthalate to result in an active ingredient-containing dry adhesive layer of 100 g/m$^2$. This layer is laminated on the adhesive side with the previously fabricated acrylate copolymer layer (adhesive layer onto adhesive layer) so that a continuous, two-layer matrix is produced. Detachment of the protective sheet produces an adhesive system which can be stuck with the polyacrylate side onto the skin. The system can be cut to the required size by suitable cutting devices.

EXAMPLE 2

A solution of poly(2-ethylhexyl acrylate-co-vinyl acetate-co-2-hydroxyethyl acrylate-co-2,3-epoxypropyl methacrylate), 30% (w/w) in ethyl acetate is coated in a layer thickness of about 65-70 μm onto a siliconized polyethylene terephthalate sheet (100 μm thick) and dried in the open at 25° C. for 2 hours to result in an adhesive layer of 20 g/m$^2$. In a separate operation, 1.5 g of fentanyl base, 70 g of polyisobutylene 100, 28 g of polyisobutylene 10, 100 g of methyl ethyl ketone and 200 g of n-heptane are made into a viscous solution and then stirred for 2 hours. This phase is coated with a layer thickness of about 500 μm onto a 15 μm-thick sheet of polyethylene terephthalate to result in an active ingredient-containing dry adhesive layer of 100 g/m$^2$.

This layer is laminated on the adhesive side with the previously fabricated acrylate copolymer layer (adhesive layer onto adhesive layer) so that a continuous, two-layer matrix is produced. Detachment of the protective sheet produces an adhesive system which can be stuck with the polyacrylate side onto the skin. The system can be cut to the required size by suitable cutting devices.

The invention claimed is:

1. A transdermal therapeutic system comprising:
at least one active pharmaceutical ingredient;
a polymer-based layer which is remote from the skin; and
an adhesive skin-contact layer which is adjacent to the polymer-based layer remote from the skin and is based on acrylate copolymers;
wherein a coating weight of the polymer-based layer remote from the skin is at least 80 g/m$^2$ and a coating weight of the skin-contact layer is not more than 50 g/m$^2$; and
wherein the at least one active pharmaceutical ingredient is present in both the polymer-based layer remote from the skin and the skin-contact layer.

2. The transdermal therapeutic system as claimed in claim 1;
wherein the mass per area of the polymer-based layer remote from the skin is 100-200 g/m$^2$.

3. The transdermal therapeutic system as claimed in claim 1;
wherein the mass per area of the skin-contact layer is 20-30 g/m$^2$.

4. The transdermal therapeutic system as claimed in claim 1;
wherein the ratio of the mass per area of the polymer-based layer remote from the skin to that of the skin-contact layer is at least 2:1.

5. The transdermal therapeutic system as claimed in claim 4;
wherein the ratio is from 3:1 to 5:1.

6. The transdermal therapeutic system as claimed in claim 1;
wherein, after production of the system and diffusion equalization, a majority of the at least one active ingredient is located in the skin-contact layer.

7. The transdermal therapeutic system as claimed in claim 1;
wherein the acrylate copolymers of the skin-contact layer comprise at least one monomer unit selected from the group consisting of acrylic acid, methacrylic acid, acrylic esters, and methacrylic esters.

8. The transdermal therapeutic system as claimed in claim 1;
wherein the acrylate copolymers of the skin-contact layer additionally comprise vinyl acetate.

9. The transdermal therapeutic system as claimed in claim 1;
wherein the at least one active ingredient is selected from the group of analgesics, bronchodilators, antidiabetics, vasodilators, anticraving agents, and antiparkinson agents.

10. The transdermal therapeutic system as claimed in claim 9;
wherein the at least one active ingredient is an analgesic.

11. The transdermal therapeutic system as claimed in claim 10;
wherein at least one of the active ingredients is an opioid.

12. The transdermal therapeutic system as claimed in claim 11;
wherein the opioid is fentanyl and/or one of its derivatives.

13. The transdermal therapeutic system as claimed in claim 12;
wherein the fentanyl derivative is alfentanil, sufentanil, or remifentanil.

14. A process for producing a transdermal therapeutic system as claimed in claim 1, comprising:
forming a mixture by mixing the at least one active ingredient, which is dissolved in a suitable volatile solvent or solvent mixture, with a polymer composition which is intended for the polymer-based layer remote from the skin;
forming the the polymer-based layer remote from the skin by:
applying the mixture uniformly in a layer thickness of at least 200 μm to a siliconized plastic sheet;
drying and evaporation of the solvent; and laminating the adhesive skin-contact layer onto the polymer-based layer remote from the skin in such a way that the active ingredient-containing polymer-based layer remote from the skin and the adhesive skin-contact layer are in contact with one another.

15. The process as claimed in claim 14;
wherein the polymer-based layer remote from the skin and the skin-contact layer are laminated together in such a way that migration of the at least one active ingredient out of the former into the latter is made possible.

16. The process as claimed in claim 14;
wherein the mass per area of the polymer-based layer remote from the skin is 100-200 g/m$^2$ and the mass per area of the skin-contact layer is 20-30 g/m$^2$.

17. The process as claimed in claim 16;
wherein the ratio of the mass per area of the polymer-based layer remote from the skin to that of the skin-contact layer is at least 2:1.

18. The process as claimed in claim 17;
wherein the ratio is from 3:1 to 5:1.

19. The process as claimed in claim 14;
wherein the at least one active ingredient is fentanyl or a fentanyl derivative.

20. The process as claimed in claim 19;
wherein the fentanyl derivative is alfentanil, sufentanil, or remifentanil.

21. A transdermal therapeutic system for administering at least one active pharmaceutical ingredient, with a daily dose in a range of from 1 mg to 500 mg, comprising:
a polymer-based layer which is remote from the skin; and
an adhesive skin-contact layer which is adjacent to the polymer-based layer remote from the skin and is based on acrylate copolymers;
wherein a mass per area of the polymer-based layer remote from the skin is at least 80 g/m$^2$ and a mass per area of the skin-contact layer is not more than 50 g/m$^2$; and
wherein the at least one active pharmaceutical ingredient is present in both the polymer-based layer remote from the skin and the skin-contact layer.

22. A transdermal therapeutic system for administering at least one active pharmaceutical ingredient, with a daily dose not exceeding 30 mg, comprising:
a polymer-based layer which is remote from the skin; and
an adhesive skin-contact layer which is adjacent to the polymer-based layer remote from the skin and is based on acrylate copolymers;
wherein a coating weight of the polymer-based layer remote from the skin is at least 80 g/m$^2$ and a coating weight of the skin-contact layer is not more than 50 g/m$^2$; and
wherein the at least one active pharmaceutical ingredient is present in both the polymer-based layer remote from the skin and the skin-contact layer.

\* \* \* \* \*